United States Patent [19]

Brannigan et al.

[11] 4,116,673

[45] Sep. 26, 1978

[54] 1-ALKYL-3-ARYL-4-PYRAZOLECARBOXYLATES

[75] Inventors: Lawrence H. Brannigan, Creve Coeur; John E. Franz, Crestwood; Robert K. Howe, Bridgeton, all of Mo.

[73] Assignee: Monsanto Company, St. Louis, Mo.

[21] Appl. No.: 715,011

[22] Filed: Aug. 18, 1976

Related U.S. Application Data

[63] Continuation-in-part of Ser. No. 645,181, Dec. 29, 1975, abandoned.

[51] Int. Cl.$^2$ ...................... A01N 9/22; C07D 231/14
[52] U.S. Cl. ............................................. 71/92; 548/378
[58] Field of Search ...................... 71/92; 260/310 R; 548/378

[56] References Cited

PUBLICATIONS

Baumes et al., Chemical Abstracts, vol. 82, 125316g, 1975.
Komendantov et al., Chemical Abstracts, vol. 82, 1975, 111337c.
Carlsson et al., Chemical Abstracts, 42692w, vol. 83, 1975.
Bastide et al., Chemical Abstracts, 111207c, vol. 78, 1973.
Bastide et al, Chem. Abst., vol. 74, 1971, 141630v.
Auwers et al., Ber. 1933, p. 1205.
Rojahn et al., Ber. 1926, pp. 607–611.

*Primary Examiner*—Natalie Trousof
*Assistant Examiner*—Jane T. Fan
*Attorney, Agent, or Firm*—Richard H. Shear; Donald W. Peterson

[57] ABSTRACT

This invention relates to novel pyrazole carboxylates having the formula

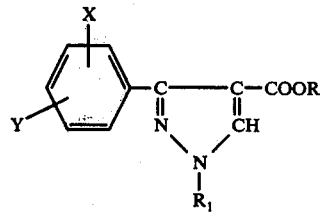

and their use as herbicides.

15 Claims, No Drawings

1-ALKYL-3-ARYL-4-PYRAZOLECARBOXYLATES

This application is a continuation-in-part of Ser. No. 645,181, filed Dec. 29, 1975, now abandoned.

This invention relates to novel pyrazolecarboxylates having the formula

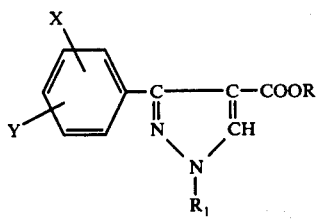
(A)

wherein R is selected from the group consisting of hydrogen, agriculturally acceptable cations, alkyl having from 1 to 8 carbon atoms, phenoxy lower alkyl, chlorinated allyl lower alkylthio lower alkyl and tetrafluorocyclobutyl methyl; $R_1$ is selected from the group consisting of hydrogen and lower alkyl; and X and Y are independently selected from the group consisting of hydrogen, trifluoromethyl, halo, lower alkyl and lower alkoxy; provided that X, Y and R may not simultaneously be hydrogen.

As used herein the term "lower alkyl" or "lower alkoxy" is meant to include those alkyl or alkoxy radicals having from 1 to 3 carbon atoms, inclusive.

The term agriculturally acceptable cations is understood to mean those cations which are commonly used in herbicidal compositions to form the salt of the free acid, including but not limited to the alkali metal, substituted amine and ammonium cations.

A novel aspect of the present invention includes the preparation of the novel pyrazolecarboxylates of the above formula in accordance with the following reaction

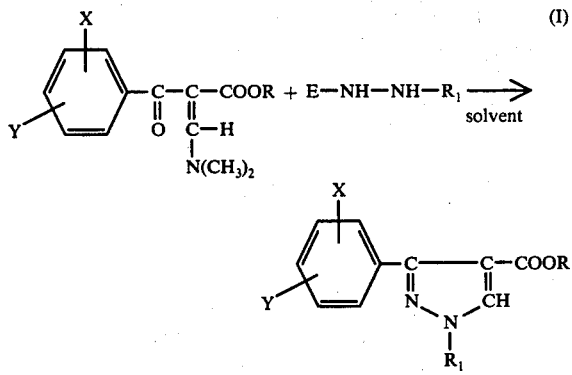
(I)

In the above reaction E may be hydrogen or carboethoxy, e.g.,

R, $R_1$, X and Y are as previously defined. The specific solvent utilized is within the skill of the art, however, ethyl ether or acetic acid are preferred.

In preparing pyrazolecarboxylates of the invention in which $R_1$ is ethyl or propyl, E in Equation I above should be carboethoxy and preferably the reaction should proceed in acetic acid. More specifically, said pyrazolecarboxylates of the invention may be prepared by preparing a solution containing equimolar quantities of the appropriate propenoic acid ester and the appropriate alkyl carbazate in acetic acid. The solution is then heated at reflux for a time sufficient to complete the reaction, usually 1 to 2 hours. After removing the solvent by evaporation under reduced pressure, the residue is dissolved in ether and washed free of acetic acid with aqueous $NaHCO_3$. After the ether solution is dried, filtered and concentrated, the more volatile impurities are removed by Kugelrohr distillation.

The following examples are presented to more particularly illustrate the preparation of the novel pyrazolecarboxylates of the invention and are not intended as a restriction of the scope of the invention. Temperatures are understood to be in degrees Centigrade (° C.).

EXAMPLE 1

To a stirred solution of 6.30 g. (0.02 mol) of ethyl 2-(α,α,α-trifluoro-m-toluoyl)-3-dimethylaminopropenoate in 50 ml. of ethyl ether cooled to −10° was added 3.3 g. of ethyl 3-ethylcarbazate (0.02 mol) assuming 80% purity. The ether was distilled off and replaced with 30 ml. of ethanol. The ethanol solution was heated at reflux for 4 hours. Glacial acetic acid (10 ml) was added and the solution heated at reflux. After 2 hours all starting material had been consumed. The solvent was removed under reduced pressure. The residual oil was dissolved in 100 ml. of ether and the solution washed with water, and 5% $NaHCO_3$ until free of acetic acid, again with water, then dried ($MgSO_4$), filtered and concentrated to 5.79 g. viscous oil which resisted crystallization from ethyl ether, hexane, pentane, and $Et_2O$-hexane, $Et_2O$-pentane mixtures.

The product was determined by NMR to be

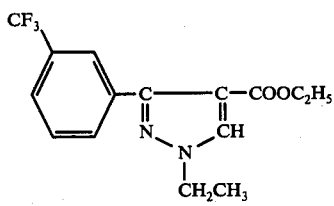

Anal. Calc'd. C, 57.69; H, 4.84; F, 18.25; N, 8.97. Found C, 57.63; H, 4.76; F, 18.27; N, 8.82.

EXAMPLE 2

To 4.94 g. (0.02 mol) ethyl 2-benzoyl-3-dimethylaminopropenoate dissolved in 50 ml. of ethanol was added 3.0 g of ethyl isopropylcarbazate with 1.5 ml. of acetic acid. An additional 25.0 ml. of acetic acid was added and the solution heated to reflux for about 18 hours. The solvent was removed by evaporating and the resulting oil taken up in 100 ml. of ether and washed with water, HCl (5%), water, saturated $NaHCO_3$, water and then dried over $MgSO_4$, filtered and concentrated. Dry column chromatography on 270 g. Silica gel-G of 4.15 g of the oil gave two components developed with a 1:4 ethyl ether:pentane solution. Evaporative distillation gave 1.30 g. of a compound having the following formula

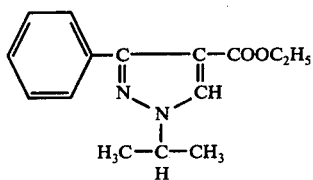

Anal. Calc'd: C, 69.74; H, 7.02; N, 10.84 Found: C, 69.83; H, 7.05; N, 10.74.

EXAMPLE 3

A mixture of 0.025 mol of ethyl 2-(m-chlorobenzoyl)-3-dimethylaminopropenoate and 0.025 mol of ethyl 3-isopropylcarbazate in 25 ml. of acetic acid was heated to reflux for 1.5 hours and allowed to settle overnight at room temperature. After removing the solvent by distillation, the residue was dissolved in 200 ml. of ether and the ether solution washed with water, then with a saturated solution of $NaHCO_3$ until free of acetic acid. After drying, filtering and concentrating, 7.27 g of an orange liquid remained. Upon evaporative distillation, 4.0 g. was obtained of a compound having the formula

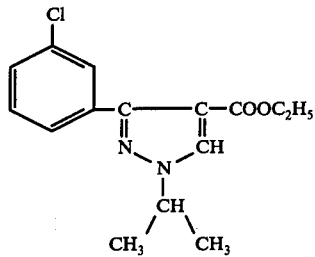

Anal. Calc'd. C, 61.54; H, 5.85; Cl, 12.11; N, 9.57. Found C, 61.60; H, 5.81; Cl, 11.92; N, 9.50.

Preparation of pyrazolecarboxylates in which $R_1$ is hydrogen or methyl may be accomplished as follows:

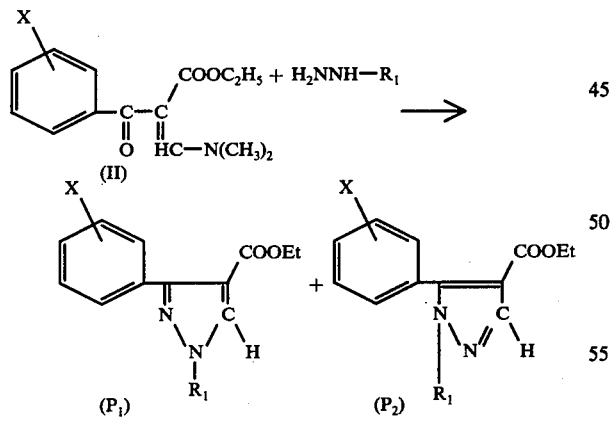

More specifically, a solution of 0.005 to 0.020 moles of the appropriate propenoic acid ester in 30–50 ml. of a solvent, preferably ethyl ether, is cooled in an ice-methanol bath with magnetic stirring to 0° to −20° C. An equimolar amount of the appropriate hydrazine in 10–20 ml. of ether is added dropwise in 10–15 minutes. The reaction is complete within 5–60 minutes. The ether is washed with 5% HCl, dried, filtered and evaporated to an oil which shows two products on glc. Isomer $P_1$ is about 90% of the product. The two isomers are separated either by fractional crystallization or column chromatography. Note that in Equation II above E is hydrogen.

The following examples are presented to further illustrate the preparation of the novel pyrazolecarboxylates of the invention and are not intended as a restriction of the scope of the invention. As in the above examples, temperatures are understood to be in degrees Centigrade (° C.).

EXAMPLE 4

A solution of 1.92 g (0.005 mol) of ethyl 2-(3', 5'-bis-trifluoromethylbenzoyl)-3-dimethylaminopropenoate in 30 ml. of ether was cooled to −20°. After heating to reflux, a solution of 0.5 g of methyl hydrazine in 10 ml. of ether was added dropwise in 30 minutes with rapid stirring. To this solution was added a reaction mixture formed by adding dropwise a solution of 0.5 g of methyl hydrazine in ether to a solution of 1.92 g of the propenoate in 30 ml. of ether at −20°. Upon washing the combined solutions with water and 5% HCl, drying, filtering and concentrating, 4.0 g of a colorless oil was obtained. This oil was then dissolved in pentane. Overnight crystals formed having a structure as follows:

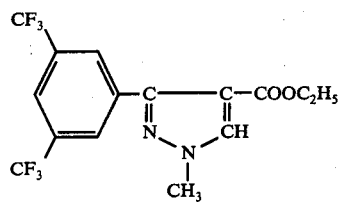

Anal. Calc'd. C, 59.99; H, 5.63; F, 16.75; N, 8.23. Found C, 59.84; H, 5.68; F, 16.64; N, 8.40.

EXAMPLE 5

A solution of 5.63 g of ethyl 2-(m-chlorobenzoyl)-3-dimethylaminopropenoate (0.02 mol) in 50 ml. ethyl ether was cooled to −10°. A solution of 2.4 ml. of 98% methyl hydrazine in 15 ml. of ether was added dropwise in 10 minutes. The mixture was stirred at room temperature for 30 minutes and washed with 5% HCl, dried ($MgSO_4$) and filtered and concentrated to a slightly yellow oil. The oil was crystallized twice from hexane to give 2.50 g of slightly yellow needles having the formula

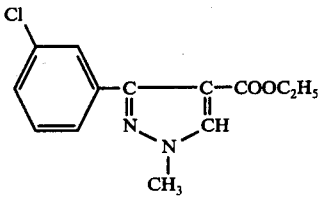

Anal. Calc'd. C, 58.99; H, 4.95; Cl, 13.39; N, 10.58. Found C, 58.94; H, 5.00; Cl, 13.44; N, 10.51.

Alternatively the pyrazolecarboxylates of the invention may be prepared in accordance with the following examples.

EXAMPLE 6

A mixture of 3.05 g of ethyl 3-(α,α,α-trifluoro-m-tolyl)-4-pyrazolecarboxylate (0.0125 mol), 10 ml. of methyl iodide and 3.4 g of anhydrous potassium carbonate in 60 ml. of anhydrous acetone was heated at 40° for 30 hours. After cooling, the solid was separated and the solution concentrated to a yellow oil. The nmr of the crude oil indicated the presence of two isomers. Upon separation by chromatography 2.2 g of a product was obtained having the formula

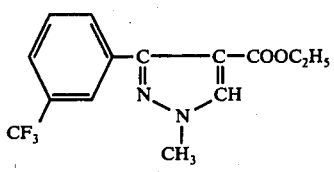

Anal. Calc'd. C, 56.38; H, 4.39; F, 19.11; N, 9.39. Found C, 56.33; H, 4.31; F, 18.96; N, 9.14.

EXAMPLE 7

A solution of 1-methyl-3-phenyl-4-pyrazolecarbonyl chloride and excess of 2,2,3,3-tetrafluorocyclobutylmethyl alcohol was heated on a steam bath for one hour. The reaction mixture was crystallized from ether-hexane to give 1.75 grams of a white solid. By NMR analysis the product was determined to be

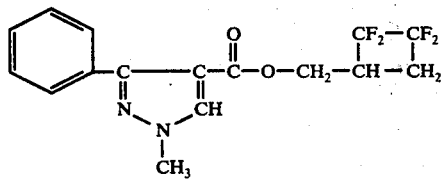

Anal. Calc'd. C, 56.14; H, 4.12; N, 8.18. Found C, 55.99; H, 4.16; N, 7.93.

EXAMPLE 8

A solution of 18.0 grams of 1-methyl-3-($\alpha,\alpha,\alpha$-m-tolyl)-4-pyrazolecarboxylic acid ethyl ester and 24 grams of sodium hydroxide in 150 ml. of a 50% ethanol solution was heated at reflux for 2 hours. The reaction mixture was concentrated under vacuum and acidified with HCl to give 14.6 grams of a white solid. The solid was recrystallized from ether-methanol to give a white solid having the structure

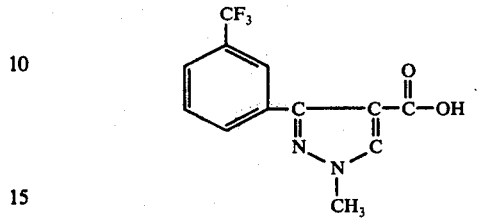

Anal. Calc'd. C, 53.34; H, 3.36; N, 10.37. Found C, 53.24; H, 3.31; N, 10.37.

EXAMPLE 9

A solution of 2.0 g (0.01 mol) of 1-methyl-3-phenyl-4-pyrazolecarboxylic acid and 100 ml. of a 0.1000 N potassium hydroxide solution (Fisher certified) was stirred at room temperature for 64 hours. The reaction mixture was concentrated under vacuum at 50° to give 2.2 g (92%) of a white solid having the structure

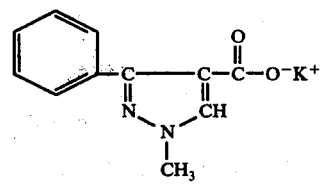

Anal. Calc'd. C, 54.98; H, 3.78; N, 11.66. Found C, 54.72; H, 3.76; N, 11.68.

In accordance with the procedures described above the following compounds have been prepared.

Table I

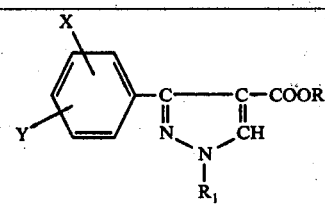

| Example | Compound | | | | Analysis | | | | | |
|---|---|---|---|---|---|---|---|---|---|---|
| | R | $R_1$ | X | Y | | C | H | F | N | Cl |
| 10 | $C_2H_5$ | Isopropyl | 3-$CF_3$ | H | Calc'd | 58.89 | 5.25 | 17.47 | 8.58 | |
| | | | | | Found | 59.11 | 5.12 | 17.31 | 8.62 | |
| 11 | $C_2H_5$ | $CH_3$ | 4-Cl | H | Calc'd | 58.99 | 4.95 | | 10.58 | 13.39 |
| | | | | | Found | 59.12 | 4.90 | | 10.55 | 13.30 |
| 12 | $C_2H_5$ | $CH_3$ | 4-$CF_3$ | H | Calc'd | 56.38 | 4.39 | 19.11 | 9.39 | |
| | | | | | Found | 56.46 | 4.50 | 19.29 | 9.31 | |
| 13 | $CF_2-CF_2$<br>\|  \|<br>$CH_2-CH-CH_2$ | $CH_3$ | 3-$CF_3$ | H | Calc'd | 49.76 | 3.19 | | 6.83 | |
| | | | | | Found | 49.72 | 3.20 | | 6.82 | |
| 14 | Cl<br>\|<br>$CH_2C=CH_2$ | $CH_3$ | 3-$CF_3$ | H | Calc'd | 52.26 | 3.51 | | 8.13 | |
| | | | | | Found | 52.53 | 3.50 | | 7.97 | |
| 15 | sec-butyl | $CH_3$ | 3-$CF_3$ | H | Calc'd | 58.89 | 5.25 | | 8.58 | |
| | | | | | Found | 58.75 | 5.21 | | 8.46 | |
| 16 | n-hexyl | $CH_3$ | 3-$CF_3$ | H | Calc'd | 61.01 | 5.97 | | 7.91 | |
| | | | | | Found | 60.84 | 6.08 | | 7.89 | |
| 17 | $CH_2CH_2-OC_6H_5$ | $CH_3$ | 3-$CF_3$ | H | Calc'd | 61.54 | 4.39 | | 7.18 | |
| | | | | | Found | 61.45 | 4.39 | | 7.10 | |
| 18 | $CH_2CH_2SC_2H_5$ | $CH_3$ | 3-$CF_3$ | H | Calc'd | 53.62 | 4.78 | | 7.82 | |
| | | | | | Found | 53.70 | 4.78 | | 8.05 | |
| 19 | $Na^+$ | $CH_3$ | H | H | Calc'd | 58.93 | 4.04 | | 12.49 | |
| | | | | | Found | 59.09 | 3.79 | | 12.60 | |
| 20 | $Li^+$ | $CH_3$ | H | H | Calc'd | 59.36 | 4.81 | | 12.58 | |

Table I-continued

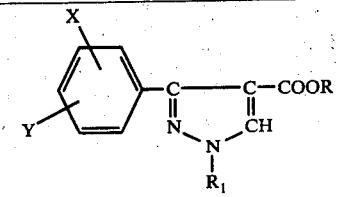

| Example | Compound R | $R_1$ | X | Y | | Analysis C | H | F | N | Cl |
|---|---|---|---|---|---|---|---|---|---|---|
| | | | | | Found | 59.35 | 4.78 | | 12.28 | |
| 21 | $Li^+$ | $CH_3$ | 3-$CF_3$ | H | Calc'd | 49.30 | 3.75 | | 9.60 | |
| | | | | | Found | 49.59 | 3.25 | | 9.51 | |
| 22 | $Na^+$ | $CH_3$ | 3-$CF_3$ | H | Calc'd | 47.01 | 3.13 | | 9.15 | |
| | | | | | Found | 46.92 | 2.72 | | 8.84 | |
| 23 | $C_2H_5$ | H | 3-$OCH_3$ | 5-$OCH_3$ | Calc'd | 60.86 | 5.84 | | 10.14 | |
| | | | | | Found | 61.09 | 5.71 | | 10.01 | |
| 24 | $C_2H_5$ | $CH_3$ | 3-$CH_3$ | H | Calc'd | 68.61 | 6.72 | | 11.35 | |
| | | | | | Found | 68.83 | 6.60 | | 11.47 | |
| 25 | $(CH_2)_3CH_3$ | $CH_3$ | 3-$CF_3$ | H | Calc'd | 58.89 | 5.25 | | 8.58 | |
| | | | | | Found | 58.62 | 4.97 | | 8.57 | |
| 26 | $C_2H_5$ | $CH_3$ | 4-$OCH_3$ | H | Calc'd | 64.60 | 6.20 | | 10.76 | |
| | | | | | Found | 64.52 | 6.23 | | 10.74 | |
| 27 | $C_2H_5$ | $CH_3$ | 3-$OCH_3$ | 5-$OCH_3$ | Calc'd | 62.06 | 6.25 | | 9.65 | |
| | | | | | Found | 62.29 | 6.42 | | 9.68 | |

In accordance with the present invention, the pyrazolecarboxylates of the foregoing formula A possess herbicidal properties. Table II summarizes results of tests conducted to determine the pre-emergent as well as the post-emergent herbicidal activity of the compounds. The pre-emergent test was conducted as follows:

A good grade of top soil was placed in aluminum pans and compacted to a depth of ⅜ to ½ inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment the pans were moved into a greenhouse bench where they were watered from below as needed to give adequate moisture for germination and growth.

Unless noted otherwise, approximately 28 days after seeding and treating, the plants were observed to determine all deviations from the normal growth habit and the results recorded. A herbicidal rating code was used to signify the extent of phytotoxicity of each species. The ratings are defined as follows:

| % Control | Rating |
|---|---|
| 0-24 | 0 |
| 25-49 | 1 |
| 50-74 | 2 |

-continued

| % Control | Rating |
|---|---|
| 75-100 | 3 |

The post-emergent tests were conducted as follows. The active ingredients are applied in spray form to 2 or 3-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately 4 weeks later the effects are observed and recorded. The results are shown in Table II in which the post-emergent herbicidal rating code is as follows:

| % Control | Rating |
|---|---|
| 0-24 | 0 |
| 25-49 | 1 |
| 50-74 | 2 |
| 75-99 | 3 |
| 100 | 4 |

The plant species utilized in these tests are identified by letter in accordance with the following legend:

| | |
|---|---|
| A Canada Thistle | G Nutsedge |
| B Cocklebur | H Quackgrass |
| C Velvetleaf | I Johnsongrass |
| D Morningglory | J Bromus tectorum |
| E Lambsquarter | K Barnyard grass |
| F Smartweed | |

TABLE II

| Compound | Rate Kg/Ha | Pre-Emergent | | | | | | | | | | | Post-Emergent | | | | | | | | | |
|---|---|---|---|---|---|---|---|---|---|---|---|---|---|---|---|---|---|---|---|---|---|---|
| | | A | B | C | D | E | F | G | H | I | J | K | A | B | C | D | E | F | G | H | I | J | K |
| 1 | *11.2 | 1 | 1 | 3 | 2 | 3 | 3 | 0 | 1 | 0 | 2 | 3 | 1 | 1 | 1 | 1 | 1 | 1 | 1 | 1 | 1 | 1 | 1 |
| | 11.2 | 1 | 0 | 3 | 0 | 3 | 1 | 0 | 0 | 0 | 1 | 3 | 1 | 1 | 1 | 1 | 1 | 0 | 0 | 0 | 0 | 0 | 0 |
| 4 | *11.2 | 1 | 0 | 1 | 1 | 3 | 1 | 0 | 0 | 0 | 1 | 3 | 2 | 2 | 1 | 2 | 1 | 1 | 0 | 0 | 0 | 0 | 0 |
| | 11.2 | 0 | 0 | 0 | 0 | 3 | 0 | 0 | 0 | 0 | 1 | 2 | 1 | 2 | 0 | 2 | 2 | 0 | 0 | 0 | 0 | 0 | 1 |
| 12 | 11.2 | 0 | 0 | 0 | 0 | 3 | 2 | 1 | 0 | 0 | 1 | 2 | 1 | 0 | 0 | 0 | 0 | 0 | 0 | 0 | 0 | 0 | 0 |
| 6 | *11.2 | 2 | 0 | 3 | 3 | 3 | 3 | 0 | 0 | 2 | 3 | 1 | 1 | 1 | 3 | 2 | 0 | 0 | 0 | 0 | 1 |
| | 11.2 | 0 | 0 | 3 | 3 | 3 | 3 | 0 | 0 | 1 | 3 | 1 | 1 | 1 | 2 | 1 | 1 | 0 | 0 | 0 | 1 | 0 |
| 13 | *11.2 | 1 | 0 | 1 | 1 | 2 | 2 | 0 | 0 | 1 | 1 | 1 | 1 | 2 | 2 | 2 | 1 | 0 | 1 | 1 | 1 | 1 |
| 14 | *11.2 | 1 | 0 | 1 | 1 | 3 | 2 | 1 | 1 | 1 | 1 | 2 | 1 | 1 | 1 | 1 | 1 | 0 | 0 | 1 | 0 | 1 |
| 15 | 11.2 | 0 | 0 | 0 | 0 | 3 | 1 | 0 | 0 | 0 | 0 | 3 | 1 | 1 | 1 | 1 | 0 | 2 | 1 | 0 | 0 | 1 | 0 |
| 16 | *11.2 | 0 | 0 | 0 | 0 | 0 | 0 | 0 | 0 | 0 | 0 | 1 | 1 | 1 | 1 | 1 | 2 | 1 | 0 | 0 | 1 | 0 | 1 |

TABLE II-continued

| Compound | Rate Kg/Ha | Pre-Emergent | | | | | | | | | | | Post-Emergent | | | | | | | | | | |
|---|---|---|---|---|---|---|---|---|---|---|---|---|---|---|---|---|---|---|---|---|---|---|---|
| | | A | B | C | D | E | F | G | H | I | J | K | A | B | C | D | E | F | G | H | I | J | K |
| 17 | *11.2 | 3 | 0 | 0 | 1 | 3 | 0 | 0 | 0 | 0 | 0 | 0 | 1 | 0 | 0 | 0 | 0 | 0 | 0 | 0 | 0 | 0 | 0 |
| 18 | *11.2 | 0 | 0 | 1 | 1 | 3 | 1 | 0 | 0 | 0 | 1 | 1 | 1 | 1 | 1 | 1 | 2 | 1 | 0 | 1 | 0 | 0 | 1 |
| 25 | 11.2 | 2 | 0 | 1 | 0 | 3 | 3 | 0 | 0 | 0 | 2 | 3 | 0 | 1 | 1 | 1 | 3 | 0 | 0 | 0 | 1 | 1 | 1 |
| 26 | *11.2 | 0 | 0 | 0 | 0 | 0 | 0 | 0 | 0 | 0 | 0 | 0 | | | | | | | | | | | |
| 26 | 11.2 | | | | | | | | | | | | 0 | 0 | 1 | 1 | 4 | 4 | 0 | 0 | 0 | 0 | 1 |

*Plants observed approximately 14 days after treatment.

In addition, each of the compounds herein have been found to be effective in controlling up to 50% of at least one or more of the plant species listed above. A preferred embodiment is those pyrazolecarboxylates in which X is CF$_3$, especially in the meta position, R is alkyl and R$_1$ is lower alkyl, especially methyl. Specifically preferred are the compounds of Examples 1 and 6.

In addition, it should be noted that many of the novel pyrazolecarboxylates of the invention selectively inhibit the growth of undesirable weeds in the presence of crop plants, such as soybeans.

For the sake of brevity and simplicity, the term "active ingredient" has been used herein and is used hereinafter to describe the pyrazolecarboxylate compounds of Formula A.

In practicing the herbicidal methods of this invention, the active ingredients can be used alone or in combination with a material referred to in the art as an adjuvant in liquid or solid form. Herbicidal formulations are prepared by admixing the active ingredient with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 to about 99 percent by weight of active ingredient.

Typical finely-divided solid carriers and inert solid extenders which can be used with the active ingredients include, for example, the talcs, natural and synthetic clays (e.g. kaolinites and attapulgite), pumice, silica, synthetic calcium and magnesium silicates, diatomaceous earth, quartz, Fuller's earth, salt, sulfur, powdered cork, powdered wood, ground corn cobs, walnut flour, chalk, tobacco dust, charcoal, volcanic ash, cottonseed hulls, wheat flour, soybean flour, tripoli and the like. Typical liquid diluents include for example: petroleum fractions such as kerosene, hexane, xylene, benzene, Diesel oil, toluene, acetone, ethylene dichloride, Stoddard solvent, alcohols such as propanol, glycols and the like.

Herbicidal formulations, particularly liquids and wettable particles, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein.

Specific surface-active agents which can be used in the herbicidal formulations of this invention are set out, for example, in Searle U.S. Pat. Nos. 2,426,417; Todd 2,655,447; Jones 2,412,510 and Lenher 2,139,276. In general, less than 50 parts by weight of the surface-active agent is present per 100 parts by weight of phytotoxic formulation.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenyl) and polyoxyethylene derivatives of the mono-higher fatty esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bis-naphthalenesulfonate and sodium N-methyl-N-(long chain acid) laurates.

Wettable powder formulations usually contain from about 5 to about 95 parts by weight of active ingredient, from about 0.25 to 25 parts by weight of wetting agent, from about 0.25 to 25 parts by weight of the dispersant and from 4.5 to about 94.5 parts by weight of inert solid extender, all parts being by weight of the total formulation. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely divided particles. The resulting concentrated aqueous suspension is characterized by its extremely small particle size, so that when diluted and sprayed coverage is very uniform.

Dusts are dense finely divided particulate formulations which are intended for application to the soil in dry form. Dusts are characterized by their free-flowing and rapid settling properties so that they are not readily windborne to areas where they are of no value. Dusts contain primarily an active ingredient and a dense, free-flowing finely divided particulate extender. However, their performance is sometimes aided by the inclusion of a wetting agent such as those listed hereinbefore under wettable powder compositions and convenient in manufacture frequently demands the inclusion of an inert, absorptive grinding aid. Suitable classes of grinding aids are natural clays, diatomaceous earth and synthetic minerals derived from silica and silicate. Preferred grinding aids include attapulgite clay, diatomaceous silica, synthetic fine silica and synthetic calcium and magnesium silicates.

The inert finely divided solid extender for the dusts can be either of vegetable or mineral origin. The solid extenders are characterized by possessing relatively low surface areas and are poor in liquid absorption. Suitable inert solid extenders for herbicidal dusts include micaceous talcs, pyrophyllite, dense kaolin clays, ground calcium phosphate rock and phyllite, and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Emulsifiable oil formulations are usually solutions of active ingredient in water-immiscible or partially water-immiscible solvents together with a surface-active agent. Suitable solvents for the active ingredient of this invention include hydrocarbons and water-immiscible ethers, esters or ketones. Suitable surface-active agents are anionic, cationic and non-ionic such as alkyl aryl polyethoxy alcohols, polyethylene sorbitol or sorbitan fatty acid esters, polyethylene glycol fatty esters, fatty alkyllol amide condensates, amine salts of fatty alcohol sulfates together with long chain alcohols and oil soluble petroleum sulfonates or mixtures thereof. The emulsifiable oil formulations generally contain from about 5 to 95 parts active ingredient, about 1 to 50 parts surface active agent and about 4 to 94 parts solvent, all parts being by weight based on the total weight of the emulsifiable oil.

Granules are physically stable particulate formulations comprising active ingredient adhering to or distributed through a basic matrix of an inert, finely divided particulate extender. In order to aid leaching of the active ingredient from the particulate, a surface active agent such as those listed hereinbefore under wettable powders can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely divided clays such as kaolin clays, hydrated attapulgite or bentonitic clays. These extenders are sprayed or blended with the active ingredient to form the herbicidal formulations.

The mineral particles which are used in the herbicidal formulations usually have a size range of 10 to 100 mesh, but preferably such that a large majority of the particles have from 14 to 60 mesh with the optimum size being from 20 to 40 mesh. Clay having substantially all particles between 14 and 80 mesh and at least about 80 percent between 20 and 40 mesh is particularly preferred for use in the herbicidal formulations. The term "mesh" as used herein means U.S. Sieve Series.

The granular herbicidal formulations generally contain from about 5 parts to about 30 parts by weight of active ingredient per 100 parts by weight of clay and 0 to about 5 parts by weight of surface-active agent per 100 parts by weight of particulate clay. The preferred granular formulations contain from about 10 parts to about 25 parts by weight of active ingredient per 100 parts by weight of clay.

The herbicidal formulations can also contain other additaments, for example, fertilizers, plant growth regulants, pesticides and the like used as adjuvant or in combination with any of the above-described adjuvants.

When operating in accordance with the present invention, effective amounts of the active ingredients are applied to the plant system. By application to the "plant system" is meant the application of the active ingredient in or on soil or plant growth media and/or applied to above ground portions of plants in any convenient fashion. Application to the soil or growth media can be carried out by simply mixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. powder dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The application of an effective amount of the active ingredients of this invention to the soil or growth media and/or plant is very important for the practice of one embodiment of the present invention. The exact amount of active ingredient to be employed is dependent upon such factors as the plant species and stage of development thereof, the specific soil and depth at which the active ingredients are distributed in the soil and the amount of rainfall as well as the specific active ingredient employed. In foliar treatment for the modification of vegetative growth, the active ingredients are applied in amounts greater than 1.12 kilograms and up to about 28 or more kilograms per hectare. In applications to soil for the modification of the germination or subsequent growth of seeds or vegetative propagules or growth of established vegetation, the active ingredients are applied in amounts from above 1.12 to about 56 or more kilograms per hectare. Generally, application amounts of 5.6 kilograms or more per hectare are preferred. It is believed that one skilled in the art can readily determine from the teachings of this specification the general procedure for any application.

In summary, in general the active ingredients may be formulated with the active ingredient in minor or major proportions in accordance with the table below:

| Type of Formulation | Concentration of Active Ingredient |
|---|---|
| 1. Granules of relatively large particle size | 5 to 50% |
| 2. Powdery dusts | .2 to 90% |
| 3. Wettable powders | 2 to 90% |
| 4. Emulsifiable concentrates | 5 to 95% |
| 5. Solutions | .01 to 95% |
| 6. One of the less common types of formulations depending on the desired mode of application | .01 to 95% |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

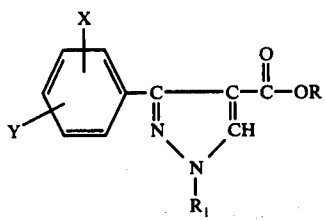

wherein R is selected from the group consisting of hydrogen and its agriculturally acceptable cations, alkyl having from 1 to 8 carbon atoms, phenoxy lower alkyl, lower alkyl thio lower alkyl and tetrafluorocyclobutylmethyl; $R_1$ is lower alkyl; and X and Y are independently selected from the group consisting of hydrogen, trifluoromethyl, halo, lower alkyl and lower alkoxy; provided that X, Y and R may not simultaneously be hydrogen.

2. A compound in accordance with claim 1 wherein R is an alkyl having from 1 to 8 carbon atoms; X is trifluoromethyl and Y is hydrogen.

3. A compound in accordance with claim 2 wherein said trifluoromethyl is in the meta position.

4. A compound in accordance with claim 3 which is 1-methyl-3-(m-trifluoromethylphenyl)-4-carbethoxypyrazole.

5. A method of preventing the growth of undesirable plants which comprises applying to the plant system a herbicidally effective amount of a compound having the formula

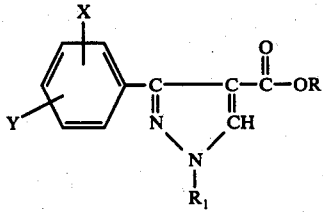

wherein R is selected from the group consisting of hydrogen and its agriculturally acceptable cations, alkyl having from 1 to 8 carbon atoms, phenoxy lower alkyl, lower alkyl thio lower alkyl and tetrafluorocyclobutylmethyl; $R_1$ is selected from the group consisting of hydrogen and lower alkyl; and X and Y are independently selected from the group consisting of hydrogen, trifluoromethyl, halo, lower alkyl and lower alkoxy; provided that X, Y and R may not simultaneously be hydrogen.

6. A method in accordance with claim 5 wherein R is alkyl having from 1 to 8 carbon atoms; $R_1$ is lower alkyl; X is trifluoromethyl and Y is hydrogen.

7. A method in accordance with claim 6 wherein said trifluoromethyl is in the meta position.

8. A method in accordance with claim 7 wherein said compound is 1-methyl-3-(m-trifluoromethylphenyl)-4-carbethoxypyrazole.

9. A herbicidal composition comprising a herbicidal adjuvant and a herbicidally effective amount of a compound having the formula

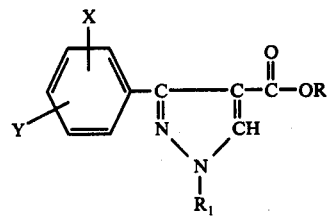

wherein R is selected from the group consisting of hydrogen and its agriculturally acceptable cations, alkyl having from 1 to 8 carbon atoms, phenoxy lower alkyl, lower alkyl thio lower alkyl and tetrafluorocyclobutylmethyl; $R_1$ is lower alkyl; and X and Y are independently selected from the group consisting of hydrogen, trifluoromethyl, halo, lower alkyl and lower alkoxy; provided that X, Y and R may not simultaneously by hydrogen.

10. A composition in accordance with claim 9 wherein R is an alkyl having from 1 to 8 carbon atoms; X is trifluoromethyl and Y is hydrogen.

11. A composition in accordance with claim 10 wherein said trifluoromethyl is in the meta position.

12. A composition in accordance with claim 11 wherein said compound is 1-methyl-3-(m-trifluoromethylphenyl)-4-carbethoxypyrazole.

13. A compound of the formula

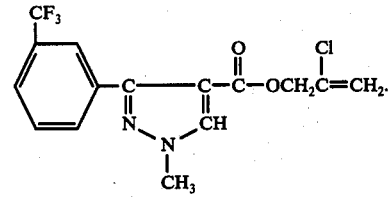

14. A method of preventing the growth of undesirable plants which comprises applying to the plant system a herbicidally effective amount of a compound having the formula

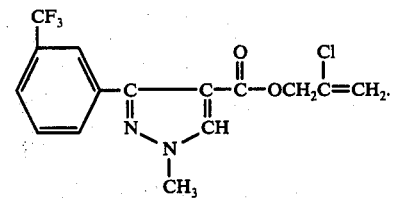

15. A herbicidal composition comprising a herbicidal adjuvant and a herbicidally effective amount of a compound having the formula

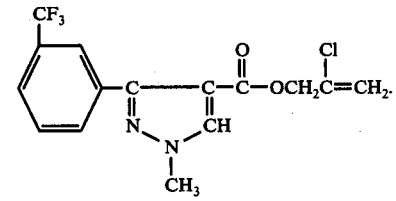

* * * * *